United States Patent [19]

Adams, Jr.

[11] 4,344,890

[45] Aug. 17, 1982

[54] AQUEOUS FUNGICIDAL FORMULATIONS AND THEIR PREPARATION

[76] Inventor: John B. Adams, Jr., R.D. #2, Box 40, Hockessin, Del. 19707

[21] Appl. No.: 259,955

[22] Filed: May 4, 1981

Related U.S. Application Data

[63] Continuation of Ser. No. 143,816, Apr. 23, 1980, abandoned.

[51] Int. Cl.$^3$ ............................ C07F 11/00; C07F 3/06
[52] U.S. Cl. .............................. 260/429 K; 260/429.9; 424/286
[58] Field of Search ........................ 260/429 K, 429.9; 424/286

[56] References Cited

U.S. PATENT DOCUMENTS

| | | | |
|---|---|---|---|
| 2,974,156 | 3/1961 | Sobatzki | 260/429 K |
| 3,173,832 | 3/1965 | Harris | 260/429 K X |
| 3,536,742 | 10/1970 | Noveroske | 260/429 K |
| 3,856,836 | 12/1974 | Boogaart et al. | 260/429 K |
| 3,869,486 | 3/1975 | Boogaart et al. | 260/429 K |
| 4,217,293 | 8/1980 | Adams | 260/429 K |

*Primary Examiner*—Helen M. S. Sneed

[57] ABSTRACT

A stable aqueous composition of maneb which includes a soluble zinc salt and formaldehyde.

9 Claims, No Drawings

AQUEOUS FUNGICIDAL FORMULATIONS AND THEIR PREPARATION

This is a continuation of application Ser. No. 143,816, filed Apr. 23, 1980, now abandoned.

BACKGROUND OF THE INVENTION

This invention relates to the preparation of stable formulations of manganese (II) ethylenebis-(dithiocarbamate) (maneb) and, more particularly, to the preparation of aqueous formulations of maneb having unexpectedly low concentrations of ethylenethiourea (ETU).

Maneb is a known important fungicide, but the compound is unstable and tends to decompose. Decomposition products, such as ethylenethiourea (ETU), appear in freshly made maneb and increase in concentration during periods of storage.

Although much work has been done which relates to improving the stability of maneb, there are no known references which teach the present invention.

L. Donev [Khimiyai industriya (Sofia) 41, 100–101 (1969), No. 3], for example, teaches a method of preparing maneb of increased dithiocarbamate content in which aqueous formaldehyde is added to a manganese(II) sulfate solution. Then a solution of ammonium ethylenebis(dithiocarbamate) (amobam) is added to precipitate the maneb. ETU concentration is not discussed.

U.S. Pat. No. 3,856,836 discloses a maneb derived from a formaldehyde-treated reaction mixture. The maneb is precipitated in aqueous medium from a water-soluble salt of ethylenebis(dithiocarbamic acid) and a water-soluble manganese(II) salt. Formaldehyde is added to the reaction mixture after precipitation. The reference does not discuss ETU concentration.

U.S. Pat. No. 2,974,156 teaches that hexamethylenetetramine (HMTA) can be added to maneb to improve stability.

U.S. Pat. No. 3,173,832 teaches that paraformaldehyde can be added to maneb to improve stability and that a soluble zinc salt can reduce phytotoxicity.

Although the prior art discloses various methods of formulating maneb to improve strength and/or stability of the product, no known references discuss the preparation of maneb having a low ETU concentration, either as a dry or an aqueous product.

SUMMARY OF THE INVENTION

The present invention is a process for preparing a unique aqueous composition of maneb having an unexpectedly low concentration of ethylenethiourea consisting essentially of maneb, 0.05 to 5.0% by weight of a soluble zinc salt (on Zn basis) and 0.05 to 5.0% by weight formaldehyde.

The combination of zinc (soluble $Zn^{2+}$) and formaldehyde in aqueous medium with maneb unexpectedly retards the buildup of ETU in maneb.

DETAILED DESCRIPTION OF THE INVENTION

The maneb used in preparing the compositions of this invention can be dihydrate, anhydrous or partially dehydrated. The dihydrate form of maneb is preferred because of its higher overall stability with respect to decomposition to ETU and because it can be formulated in aqueous mixtures directly without having to dry it first.

Maneb, which has been prepared according to the process disclosed and claimed in U.S. Ser. No. 935,507, the teachings of which are incorporated herein by reference, is preferred because of its resistance to decomposition. According to that process, maneb can be prepared by reacting a soluble manganese(II) salt with disodium (nabam) or dipotassium salt of ethylenebis(dithiocarbamic acid) which has been treated with formaldehyde. As used herein, the term "nabam" is intended to include the potassium analog of disodium ethylenebis(dithiocarbamate). Alternatively, maneb can be precipitated by reacting ammonium ethylenebis(dithiocarbamate) (amobam) or plain nabam with an aqueous solution of a manganese (II) salt. Nabam is the preferred salt because it yields maneb of lower initial ETU content.

It has been noted that nabam treated with formaldehyde produces maneb of a relatively large particle size. Thus, it is preferable to precipitate the maneb in the presence of a dispersant which will cause the maneb to form and remain as small particles and reduce or eliminate the need for grinding, etc., prior to formulation.

Suitable dispersants include some of the ligninsulfonate type, such as Polyfon ® H (a sodium lignosulfonate produced by Westvaco Chemical Division, N. Charleston, South Carolina). The amount of dispersant will ordinarily depend on the nature of the dispersant. Economic considerations suggest using no more dispersant than necessary for obtaining the desired maneb particle size. Using too much dispersant could slow filtration of the maneb reaction mixture, which may necessitate other means (e.g., centrifugation) for satisfactory maneb recovery. Generally, the amount of dispersant can range from about 0.1 to 10% of the reaction mixture. Surprisingly, when nabam is used without formaldehyde, the presence of a dispersant, even though satisfactory when used with formaldehyde, may cause formation of maneb particles which are larger than if no dispersant is used at all.

The maneb concentration in the compositions of this invention can vary depending on the strength desired. For example, maneb strength can vary from about 10 to 50% by weight, with 25 to 40% by weight being the preferred concentration for economic reasons.

The use of formaldehyde with a soluble zinc salt achieves an unexpectedly low concentration of ETU when maneb is formulated as an aqueous composition. Although either formaldehyde or soluble zinc salts might contribute toward producing low ETU concentrations in fresh aqueous maneb compositions, storage studies show that a zinc salt, in the absence of formaldehyde, can actually increase ETU concentration. Even though formaldehyde alone operates to minimize ETU levels, the use of both a soluble zinc salt and formaldehyde in the composition can produce surprisingly low ETU levels in aqueous maneb.

The compositions of this invention will ordinarily contain about 0.05–5.0% by weight of zinc salt (based on Zn) and about 0.05–5.0% by weight of formaldehyde. Preferably, the compositions will contain about 0.1 to 2.5% by weight each of zinc salt and formaldehyde. Too much formaldehyde can create odor or phytotoxicity problems and too much soluble zinc salt in the composition can affect maneb stability. This invention is illustrated in a preferred embodiment in Table A and the examples which follow. The table and examples are not to be considered as limiting, but merely exemplary. The significant feature is the combined action of formaldehyde and a solution zinc salt in reducing ETU concentrations in aqueous maneb compositions.

Additional formulation ingredients, such as dispersants, anticorrosion agents, etc., as well as other fungicides, such as methyl 2-benzimidazolecarbamate (carbendazim) and 2-cyano-N-[(ethylamino)-carbonyl]-2-(methoximino)acetamide (Curzate ®), can be present as long as they do not cause ETU buildup in the formulation or react substantially with formaldehyde to the detriment of the formulation.

As used herein, the term "mancozeb" is intended to mean a complex of maneb and zinc resulting from reaction to maneb with a soluble zinc salt under wet conditions. [For a description of maneb and mancozeb, see *Pesticide Manual*, 5th Edition, edited by H. Martin and C. R. Worthing, issued by the British Crop Protection Council, pages 328 and 329.]

The term "maneb" is intended to include mancozeb when the maneb has been treated under wet conditions with a soluble salt of zinc.

TABLE A

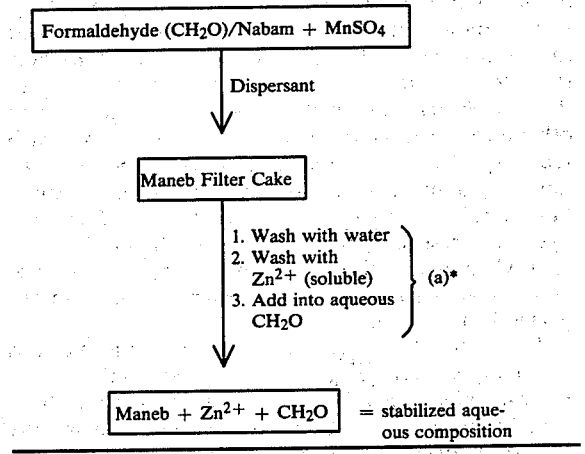

The preparation of the composition may be accomplished several ways:

(a)*
(b) Add the filter cake directly into aqueous $CH_2O + Zn^{2+}$ (soluble);
(c) Wash the filter cake with aqueous [$CH_2O + Zn^{2+}$ (soluble)] and then add to water;
(d) Wash with aqueous $CH_2O$ and add to aqueous $Zn^{2+}$ (soluble);
(e) Wash with aqueous $Zn^{2+}$ (soluble) and add to aqueous $CH_2O$.

Any other suitable variation of the above procedures, e.g., wash with aqueous $Zn^{2+}$ (soluble) and add to water simultaneously with $CH_2O$, can be used.

Further reduction in maneb particle size can be accomplished, if desired, by wet-milling. If desired, the conversion of maneb to zineb[1] during the milling process can be avoided by adding $Zn^{2+}$ (soluble) after the milling process. Wet-milling is further described in U.S. Pat. No. 3,157,486.

[1] zineb=zinc ethylenebis(dithiocarbamate).

EXAMPLE 1

TABLE B

Formaldehyde/Nabam:
Dispersant During Precipitation:
Maneb Aqueous

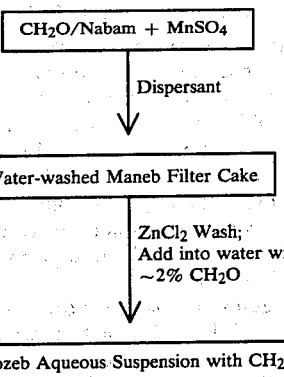

| | PPM | Aging |
|---|---|---|
| ETU | 1-2 | 1 day, room temperature (R.T.) |
| | 1 | 20 days, R.T. |

Into a flask containing a stirred $N_2$-blanketed solution of 15.2 g. of Polyfon ® H in 1160 ml. of water at 25° was simultaneously added during a 50-minute period an aqueous solution of 723.2 g. of 23% $MnSO_4$ and formaldehyde/nabam [1115 g. of 23% nabam and 40.6 g. of 37% $CH_2O$ mixed and let stand at ambient temperature for 30 minutes before beginning to use in reaction with $MnSO_4$]. After 10 minutes, the maneb was filtered off, washed with water and with 1 kg. of 7% $ZnCl_2$. The filter cake was suspended in aqueous formaldehyde such that the maneb concentration (expressed as anhydrous) was about 35% and the formaldehyde concentration was 2.2%. The zinc assay was 1.1% total and 0.9% soluble. The ETU assays are noted above.

The method of adding reactants simultaneously to a common body of water as in this example is usually referred to as a "heel process".

EXAMPLE 2

TABLE C

Formaldehyde/Nabam;
Dispersant During Precipitation;
Maneb Aqueous

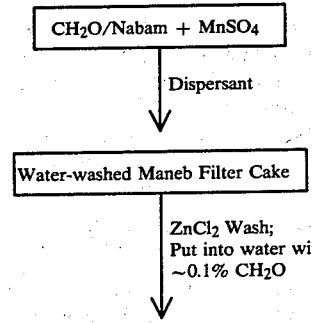

| | PPM | Aging |
|---|---|---|
| ETU | 4 | 2 days, R.T. |

TABLE C-continued

Formaldehyde/Nabam;
Dispersant During Precipitation;
Maneb Aqueous

| 2 | 22 days, R.T. |
|---|---|

The same general procedure was used as in Example 1. The final maneb mixture contained about 28% maneb (expressed as anhydrous), about 0.1% $CH_2O$, and the zinc assay was 1.3%, total, and 1.0% soluble. The ETU assays are noted above.

EXAMPLE 3

TABLE D

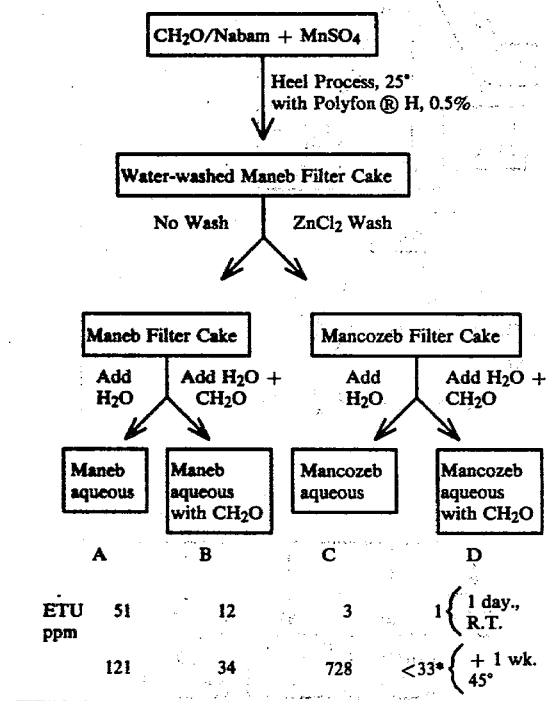

| | A | B | C | D |
|---|---|---|---|---|
| ETU ppm | 51 | 12 | 3 | 1 (1 day., R.T.) |
| | 121 | 34 | 728 | <33* (+ 1 wk. 45°) |

*This figure is unusually high because of interference peaks encountered in the liquid chromatographic method used for ETU assay. The true ETU level could possibly be as low as zero; if all the interference plus ETU is reported as ETU, the ETU level is still less than 33 ppm. Similar comments apply to other examples herein where a "<No." is reported for ETU concentration.

The same general procedure was followed as in Example 1, except the filter cakes were split at various stages as indicated to show effects of the $CH_2O$ and $ZnCl_2$ as to their absence, separate use, and combined use. Initially, $CH_2O$ and $ZnCl_2$ separately, and especially $CH_2O$ and $ZnCl_2$ combined, help reduce ETU, whereas after 1 week at 45°, the combination of $CH_2O$ and $ZnCl_2$ is more favorable. The $CH_2O$ concentration in samples B and D was about 2%.

EXAMPLE 4

TABLE E

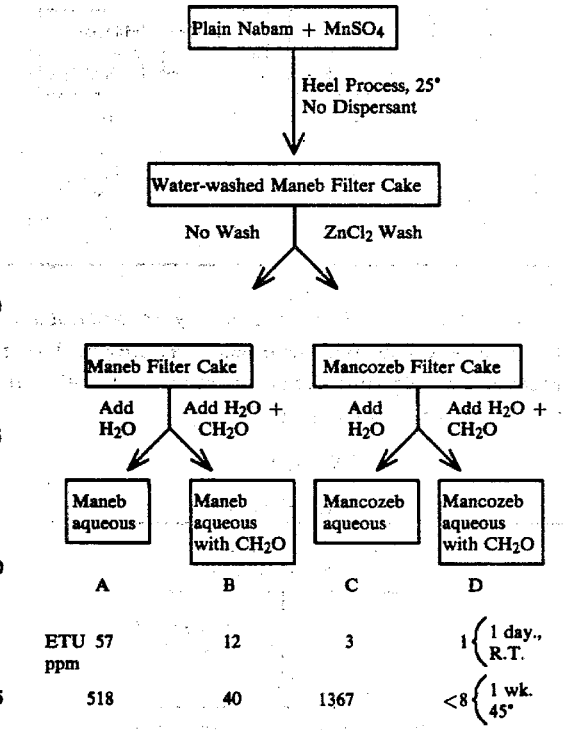

| | A | B | C | D |
|---|---|---|---|---|
| ETU ppm | 57 | 12 | 3 | 1 (1 day., R.T.) |
| | 518 | 40 | 1367 | <8 (1 wk. 45°) |

The samples were prepared generally as described in Example 3, except that plain nabam (no $CH_2O$) was used to prepare the initial maneb precipitate in the absence of a dispersant. Again, the sample (D) with both $CH_2O$ and $Zn^{2+}$ is more satisfactory.

EXAMPLE 5

TABLE F

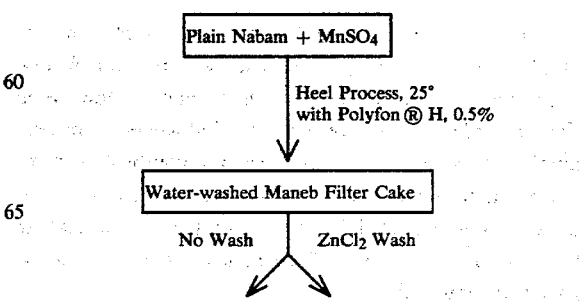

TABLE F-continued

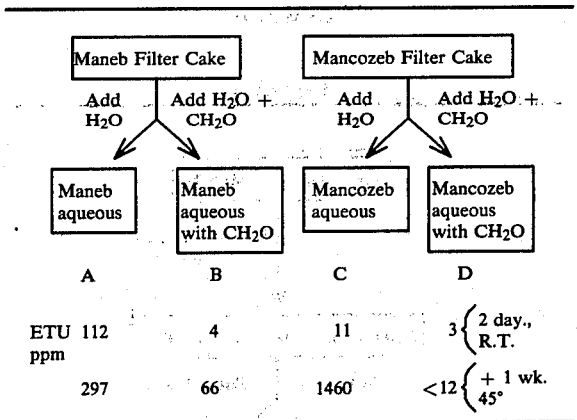

|  | A | B | C | D |
|---|---|---|---|---|
| ETU ppm | 112 | 4 | 11 | 3 { 2 day., R.T. |
|  | 297 | 66 | 1460 | <12 { +1 wk. 45° |

The samples were made generally as described in Example 4, except that dispersant was present during precipitation of maneb. Again, the sample (D) with both $CH_2O$ and $Zn^{2+}$ is more satisfactory.

EXAMPLE 6

TABLE G

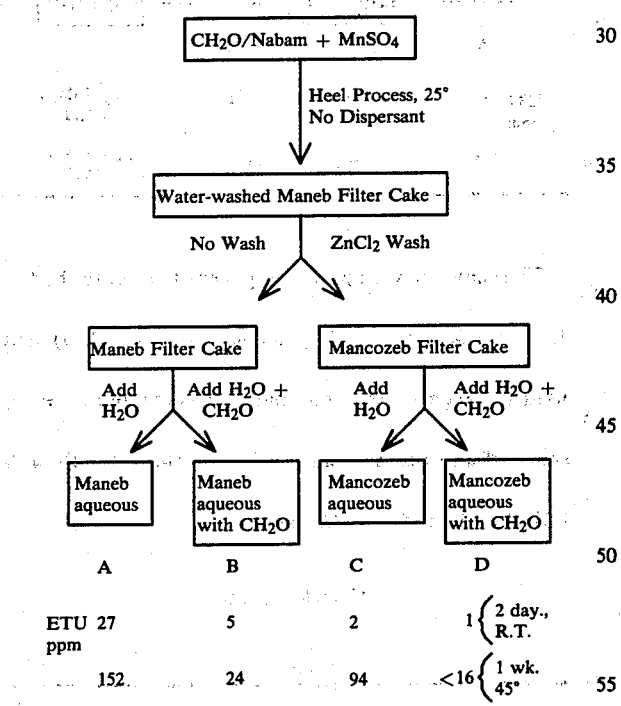

|  | A | B | C | D |
|---|---|---|---|---|
| ETU ppm | 27 | 5 | 2 | 1 { 2 day., R.T. |
|  | 152 | 24 | 94 | <16 { 1 wk. 45° |

The same general procedure was followed as in Example 3, except that no dispersant was present during precipitation. The particle size of the maneb obtained in this example was far greater than that obtained in Example 3. It is perhaps for this reason that in this example alone, the presence of $Zn^{2+}$ (in absence of $CH_2O$, sample C) has helped hold down ETU concentration during the 1-week, 45° storage of the aqueous maneb as compared to sample A.

EXAMPLE 7

TABLE H

Maneb Dihydrate vs. Maneb Anhydrous
For Maneb Aqueous Suspensions

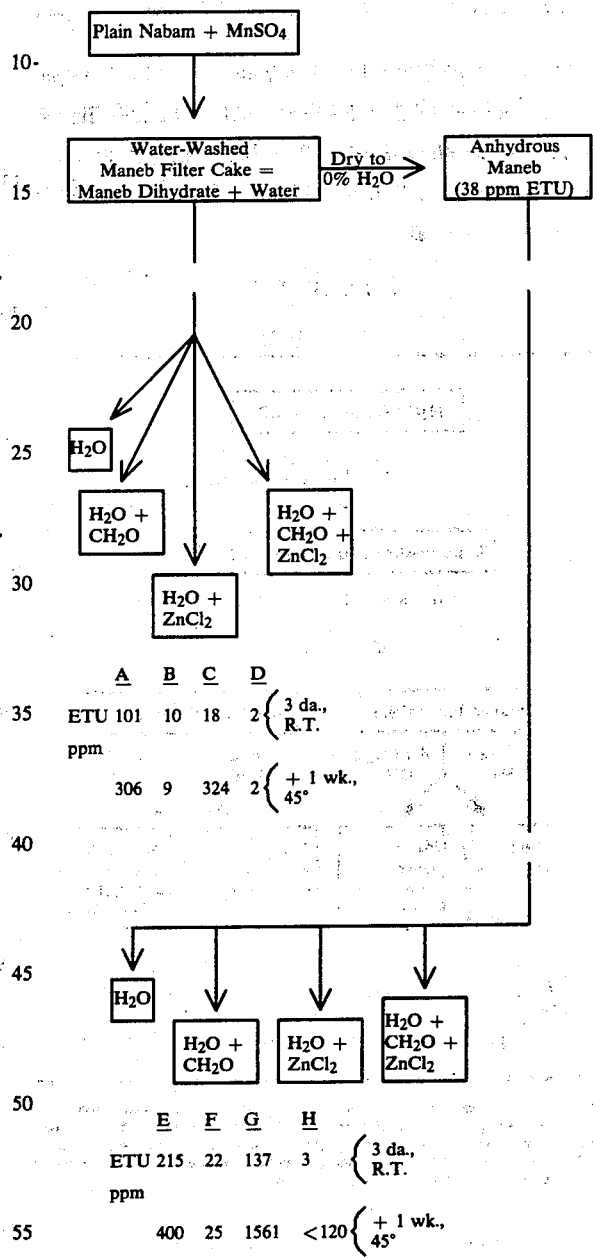

|  | A | B | C | D |
|---|---|---|---|---|
| ETU ppm | 101 | 10 | 18 | 2 { 3 da., R.T. |
|  | 306 | 9 | 324 | 2 { +1 wk., 45° |

|  | E | F | G | H |
|---|---|---|---|---|
| ETU ppm | 215 | 22 | 137 | 3 { 3 da., R.T. |
|  | 400 | 25 | 1561 | <120 { +1 wk., 45° |

In this example, maneb dihydrate was compared to anhydrous maneb in aqueous composition. In each case, the presence or absence of $ZnCl_2$ and $CH_2O$ and their combination were examined. Pressure built up during the accelerated storage of samples F, G, and H, though ETU levels were held down with $CH_2O$ and with $CH_2O/ZnCl_2$. Overall, stability is good for the samples made from maneb dihydrate.

EXAMPLE 8
TABLE I

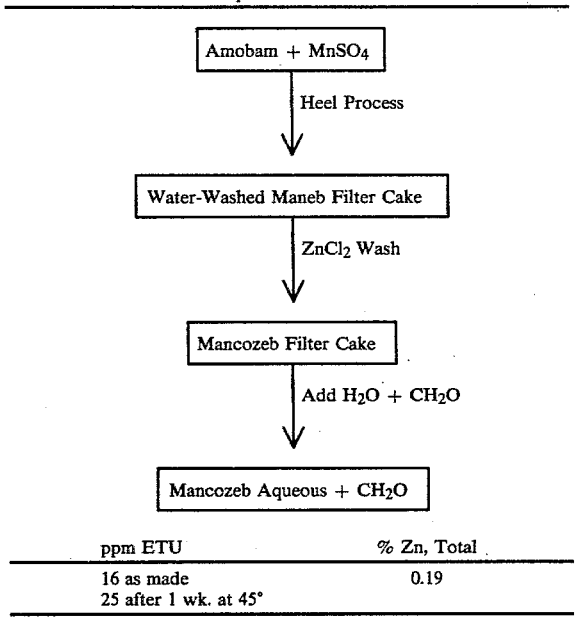

Maneb Aqueous From Amobam

| ppm ETU | % Zn, Total |
|---|---|
| 16 as made | 0.19 |
| 25 after 1 wk. at 45° | |

Amobam, as previously exemplified with nabam, can also provide low-ETU aqueous maneb when used in conjunction with $Zn^{2+}$ (soluble)+$CH_2O$. The levels of ETU obtained appear to be somewhat higher than those obtained when the maneb is derived from nabam or $CH_2O$/nabam.

What is claimed is:

1. In a process for preparing a stabilized aqueous composition of maneb by reacting a disodium, dipotassium, or diammonium salt of ethylenebis(dithiocarbamic acid) with a water-soluble manganese(II) salt in aqueous medium to precipitate maneb, and recovering the maneb, the improvement which comprises mixing the maneb in an aqueous medium with about 0.05–5.0% by weight of formaldehyde and about 0.05–5.0% by weight (based on Zn) of a soluble zinc salt.

2. The improvement of claim 1 including the additional step of treating the disodium or dipotassium salt of ethylenebis(dithiocarbamic acid) with formaldehyde prior to reaction with the water-soluble manganese(II) salt.

3. The improvement of claim 1 in which the water-soluble manganese(II) salt is reacted with the disodium salt of ethylenebis(dithiocarbamic acid).

4. The improvement of claim 1 in which the water-soluble managnese(II) salt is reacted with the diammonium salt of ethylenebis(dithiocarbamic acid).

5. A stabilized aqueous composition of maneb of low ethylenethiourea content having a maneb concentration of about 10 to 50% by weight which is prepared by the process which comprises reacting a disodium, dipotassium, or diammonium salt of ethylenebis(dithiocarbamic acid) with a water-soluble manganese(II) salt in aqueous medium to precipitate maneb, recovering the maneb and then mixing the maneb in aqueous medium with about 0.05–5.0% by weight of formaldehyde and about 0.05–5.0% by weight (based on Zn) of a soluble zinc salt.

6. The stabilized aqueous composition of claim 5 in which the disodium salt of ethylenebis(dithiocarbamic acid) is reacted with a water-soluble manganese(II) salt.

7. The stabilized aqueous composition of claim 6 in which the disodium salt of ethylenebis(dithiocarbamic acid) is treated with formaldehyde prior to reaction with the water-soluble manganese(II) salt.

8. The improvement of claim 2 in which maneb is precipitated in the presence of a dispersant.

9. The stabilized aqueous composition of claim 7 in which maneb is precipitated in the presence of a dispersant.

* * * * *